United States Patent
Schultheis et al.

(10) Patent No.: US 11,672,599 B2
(45) Date of Patent: Jun. 13, 2023

(54) ACOUSTIC PERFORMANCE MONITORING SYSTEM AND METHOD WITHIN INTRAVASCULAR LITHOTRIPSY DEVICE

(71) Applicant: Bolt Medical, Inc., Carlsbad, CA (US)

(72) Inventors: Eric Schultheis, San Clemente, CA (US); Christopher A. Cook, Laguna Niguel, CA (US)

(73) Assignee: Bolt Medical, Inc., Carlsbad, CA (US)

( * ) Notice: Subject to any disclaimer, the term of this patent is extended or adjusted under 35 U.S.C. 154(b) by 257 days.

(21) Appl. No.: 17/194,160

(22) Filed: Mar. 5, 2021

(65) Prior Publication Data
US 2021/0275247 A1 Sep. 9, 2021

Related U.S. Application Data

(60) Provisional application No. 62/987,063, filed on Mar. 9, 2020.

(51) Int. Cl.
*A61B 18/24* (2006.01)
*A61B 18/26* (2006.01)
*A61B 18/00* (2006.01)

(52) U.S. Cl.
CPC ............ *A61B 18/245* (2013.01); *A61B 18/26* (2013.01); *A61B 2018/0022* (2013.01);
(Continued)

(58) Field of Classification Search
CPC .................. A61B 18/245; A61B 18/26; A61B 2018/0022; A61B 2018/00369;
(Continued)

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

International Search Report and Written Opinion, issued by the European Patent Office for PCT/2021/XXX, dated Sep. 30, 2021.
(Continued)

*Primary Examiner* — Carl H Layno
*Assistant Examiner* — Aya Ziad Bakkar
(74) *Attorney, Agent, or Firm* — Roeder & Broder LLP; James P. Broder

(57) ABSTRACT

A catheter system and method for treating a treatment site within or adjacent to a vessel wall or a heart valve within a body of a patient includes an energy source, an inflatable balloon, an energy guide, and an acoustic sensor. The inflatable balloon is positionable substantially adjacent to the treatment site. The inflatable balloon has a balloon wall that defines a balloon interior that receives a balloon fluid. The energy guide receives energy from the energy source and guides the energy into the balloon interior. The acoustic sensor is positioned outside the body of the patient. The acoustic sensor senses acoustic sound waves generated in the balloon fluid within the balloon interior. The acoustic sensor generates a sensor signal based at least in part on the sensed acoustic sound waves.

20 Claims, 3 Drawing Sheets

(52) U.S. Cl.
CPC ............ *A61B 2018/00369* (2013.01); *A61B 2018/00696* (2013.01); *A61B 2018/00845* (2013.01); *A61B 2018/266* (2013.01); *A61B 2562/0204* (2013.01)

(58) Field of Classification Search
CPC ........... A61B 2018/00696; A61B 2018/00845; A61B 2562/0204
See application file for complete search history.

(56) References Cited

U.S. PATENT DOCUMENTS

| | | |
|---|---|---|
| 4,799,479 A | 1/1989 | Spears |
| 4,913,142 A | 4/1990 | Kittrell et al. |
| 4,955,895 A | 9/1990 | Sugiyama |
| 4,960,108 A | 10/1990 | Reichel et al. |
| 4,994,059 A | 2/1991 | Kosa et al. |
| 5,034,010 A | 7/1991 | Kittrell et al. |
| 5,041,121 A | 8/1991 | Wondrazek et al. |
| 5,104,391 A | 4/1992 | Ingle |
| 5,116,227 A | 5/1992 | Levy |
| 5,152,768 A | 10/1992 | Bhatta |
| 5,173,049 A | 12/1992 | Levy |
| 5,181,921 A | 1/1993 | Makita et al. |
| 5,200,838 A | 4/1993 | Nudelman |
| 5,290,277 A | 3/1994 | Vercimak et al. |
| 5,372,138 A | 12/1994 | Crowley |
| 5,400,428 A | 3/1995 | Grace |
| 5,422,926 A | 6/1995 | Smith |
| 5,454,809 A | 10/1995 | Janssen |
| 5,509,917 A | 4/1996 | Cecchetti |
| 5,540,679 A | 7/1996 | Fram |
| 5,562,657 A | 10/1996 | Griffin |
| 5,598,494 A | 1/1997 | Behrmann et al. |
| 5,609,606 A | 3/1997 | O'Boyle |
| 5,611,807 A | 3/1997 | O'Boyle |
| 5,697,377 A | 12/1997 | Wittkamph |
| 5,718,241 A | 2/1998 | Ben-Haim et al. |
| 5,729,583 A | 3/1998 | Tang |
| 5,772,609 A | 6/1998 | Nguyen et al. |
| 5,891,135 A | 4/1999 | Jackson et al. |
| 5,906,611 A | 5/1999 | Dodick et al. |
| 5,944,697 A | 8/1999 | Benett et al. |
| 6,080,119 A | 6/2000 | Schwarze et al. |
| 6,123,923 A | 9/2000 | Unger |
| 6,139,510 A | 10/2000 | Palermo |
| 6,186,963 B1 | 2/2001 | Schwarze et al. |
| 6,203,537 B1 | 3/2001 | Adrian |
| 6,210,404 B1 | 4/2001 | Shadduck |
| 6,339,470 B1 | 1/2002 | Papademetriou et al. |
| 6,368,318 B1 | 4/2002 | Visuri et al. |
| 6,500,174 B1 | 12/2002 | Maguire et al. |
| 6,514,203 B2 | 2/2003 | Bukshpan |
| 6,514,249 B1 | 2/2003 | Maguire |
| 6,524,251 B2 | 3/2003 | Rabiner et al. |
| 6,538,739 B1 | 3/2003 | Visuri et al. |
| 6,607,502 B1 | 8/2003 | Maguire et al. |
| 6,652,547 B2 | 11/2003 | Rabiner et al. |
| 6,666,834 B2 | 12/2003 | Restle et al. |
| 6,773,447 B2 | 8/2004 | Laguna |
| 6,849,994 B1 | 2/2005 | White et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,309,324 B2 | 12/2007 | Hayes et al. |
| 7,470,240 B2 | 12/2008 | Schultheiss et al. |
| 7,569,032 B2 | 8/2009 | Naimark et al. |
| 7,599,588 B2 | 10/2009 | Eberle et al. |
| 7,713,260 B2 | 5/2010 | Lessard |
| 7,758,572 B2 | 7/2010 | Weber et al. |
| 7,810,395 B2 | 10/2010 | Zhou |
| 7,850,685 B2 | 12/2010 | Kunis et al. |
| 7,867,178 B2 | 1/2011 | Simnacher |
| 7,972,299 B2 | 7/2011 | Carter |
| 7,985,189 B1 | 7/2011 | Ogden et al. |
| 8,162,859 B2 | 4/2012 | Schultheiss et al. |
| 8,166,825 B2 | 5/2012 | Zhou |
| 8,192,368 B2 | 6/2012 | Woodruff |
| 8,292,913 B2 | 10/2012 | Warnack |
| 8,364,235 B2 | 1/2013 | Kordis et al. |
| 8,419,613 B2 | 4/2013 | Saadat |
| 8,439,890 B2 | 5/2013 | Beyar |
| 8,556,813 B2 | 10/2013 | Cashman et al. |
| 8,574,247 B2 | 11/2013 | Adams et al. |
| 8,657,814 B2 | 2/2014 | Werneth |
| 8,709,075 B2 | 4/2014 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 8,986,339 B2 | 3/2015 | Warnack |
| 8,992,817 B2 | 3/2015 | Stamberg |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,072,534 B2 | 7/2015 | Adams et al. |
| 9,131,949 B2 | 9/2015 | Coleman et al. |
| 9,138,249 B2 | 9/2015 | Adams et al. |
| 9,138,260 B2 | 9/2015 | Miller et al. |
| 9,180,280 B2 | 11/2015 | Hawkins et al. |
| 9,220,521 B2 | 12/2015 | Hawkins et al. |
| 9,237,984 B2 | 1/2016 | Hawkins et al. |
| 9,289,132 B2 | 3/2016 | Ghaffar et al. |
| 9,289,224 B2 | 3/2016 | Adams et al. |
| 9,320,530 B2 | 4/2016 | Grace |
| 9,333,000 B2 | 5/2016 | Hakala et al. |
| 9,375,223 B2 | 6/2016 | Wallace |
| 9,421,025 B2 | 8/2016 | Hawkins et al. |
| 9,433,428 B2 | 9/2016 | Hakala et al. |
| 9,504,809 B2 | 11/2016 | Bo |
| 9,510,887 B2 | 12/2016 | Burnett |
| 9,522,012 B2 | 12/2016 | Adams |
| 9,554,815 B2 | 1/2017 | Adams et al. |
| 9,555,267 B2 | 1/2017 | Ein-gal |
| 9,566,209 B2 | 2/2017 | Katragadda et al. |
| 9,579,114 B2 | 2/2017 | Mantell et al. |
| 9,629,567 B2 | 4/2017 | Porath et al. |
| 9,642,673 B2 | 5/2017 | Adams |
| 9,662,069 B2 | 5/2017 | De Graff et al. |
| 9,687,166 B2 | 6/2017 | Subramaniam |
| 9,730,715 B2 | 8/2017 | Adams |
| 9,764,142 B2 | 9/2017 | Imran |
| 9,814,476 B2 | 11/2017 | Adams et al. |
| 9,861,377 B2 | 1/2018 | Mantell et al. |
| 9,867,629 B2 | 1/2018 | Hawkins et al. |
| 9,894,756 B2 | 2/2018 | Weinkam et al. |
| 9,955,946 B2 | 5/2018 | Miller et al. |
| 9,974,963 B2 | 5/2018 | Imran |
| 9,974,970 B2 | 5/2018 | Nuta et al. |
| 9,993,292 B2 | 6/2018 | Adams et al. |
| 10,039,561 B2 | 8/2018 | Adams et al. |
| 10,136,829 B2 | 11/2018 | Deno et al. |
| 10,149,690 B2 | 12/2018 | Hawkins et al. |
| 10,159,505 B2 | 12/2018 | Hakala et al. |
| 10,194,994 B2 | 2/2019 | Deno et al. |
| 10,201,387 B2 | 2/2019 | Grace et al. |
| 10,206,698 B2 | 2/2019 | Hakala et al. |
| 10,226,265 B2 | 3/2019 | Ku et al. |
| 10,357,264 B2 | 7/2019 | Kat-Kuoy |
| 10,405,923 B2 | 9/2019 | Yu et al. |
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |

(56) References Cited

U.S. PATENT DOCUMENTS

| | | |
|---|---|---|
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2005/0010095 A1 | 1/2005 | Stewart et al. |
| 2005/0021013 A1 | 1/2005 | Visuri |
| 2005/0080396 A1 | 4/2005 | Rental |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1* | 9/2012 | Stahmann ............ A61B 5/026 600/483 |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0116714 A1 | 5/2013 | Adams et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0180069 A1 | 6/2014 | Millett |
| 2014/0180126 A1 | 6/2014 | Millett |
| 2014/0180134 A1 | 6/2014 | Hoseit |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0336632 A1 | 11/2014 | Toth |
| 2015/0005576 A1 | 1/2015 | Diodone et al. |

(56) References Cited

U.S. PATENT DOCUMENTS

| | | |
|---|---|---|
| 2015/0039002 A1 | 2/2015 | Hawkins |
| 2015/0073430 A1 | 3/2015 | Hakala et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0276689 A1 | 10/2015 | Watanabe et al. |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-Kuoy |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0104933 A1 | 4/2019 | Stern |
| 2019/0175111 A1 | 6/2019 | Genereux et al. |
| 2019/0175300 A1 | 6/2019 | Hom |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0388002 A1 | 12/2019 | Bozsak et al. |
| 2019/0388110 A1 | 12/2019 | Nguyen et al. |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0129195 A1 | 4/2020 | McGowan et al. |
| 2020/0129741 A1 | 4/2020 | Kawwas |
| 2020/0197019 A1 | 6/2020 | Harper |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 11399346 | 1/2022 |

(56) References Cited

FOREIGN PATENT DOCUMENTS

| | | |
|---|---|---|
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A1 | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 1946712 A1 * | 7/2008 ............ A61B 18/04 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | 9902095 A1 | 1/1999 |
| WO | 1999002095 A1 | 1/1999 |
| WO | 9920189 A1 | 4/1999 |
| WO | 1999020189 A1 | 4/1999 |
| WO | WO200067648 | 11/2000 |
| WO | WO2000067648 A1 | 11/2000 |
| WO | WO0103599 A2 | 1/2001 |
| WO | 20060006169 A2 | 1/2006 |
| WO | WO2009121017 | 10/2009 |
| WO | WO2009149321 A1 | 12/2009 |
| WO | 2010042653 A1 | 4/2010 |
| WO | WO2011094379 | 8/2011 |
| WO | 20110126580 A2 | 10/2011 |
| WO | WO2012025833 | 3/2012 |
| WO | WO20120052924 A1 | 4/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 20150177790 A1 | 11/2015 |
| WO | WO2016089683 A1 | 6/2016 |
| WO | WO2016090175 | 6/2016 |
| WO | WO-2016090175 A1 * | 6/2016 ........... A61B 17/122 |
| WO | WO2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 20180175322 A1 | 9/2018 |
| WO | WO2019200201 A1 | 10/2019 |
| WO | WO2019215869 A1 | 11/2019 |
| WO | WO2019222843 | 11/2019 |
| WO | WO-2019222843 A1 * | 11/2019 ........... A61L 29/085 |
| WO | WO2020056031 | 3/2020 |
| WO | WO20200086361 A1 | 4/2020 |
| WO | WO2020089876 A1 | 5/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021067563 | 4/2021 |
| WO | WO2021086571 A1 | 5/2021 |
| WO | WO2021096922 A1 | 5/2021 |
| WO | WO2021101766 A1 | 5/2021 |
| WO | WO2021126762 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | 2022055784 | 3/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

International Search Report and Written Opinion dated Nov. 8, 2022 in PCT Application Serial No. PCT US/2022/039678.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

(56) References Cited

OTHER PUBLICATIONS

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced ShockWave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc, The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18/185,152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube—PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104,173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, dated Jan. 16, 2019.
European Search Report, for European Patent Application No. 18185152.8, dated Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Search Report and Written Opinion, issued by the EP/ISA, in PCT/US2021/048819, dated Jan. 14, 2022.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.

(56) References Cited

OTHER PUBLICATIONS

International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044 2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery of Atrial Endocardial Potential Maps From Non-contact Electrode Data." Auckland Bioengineering Institute.
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL.
Sacher et al., "Comparison of Manual Vs Automatic Annotation to Identify Abnormal Substrate for Scar Related VT Ablation." LIRYC Institute, Bordeaux University Hospital, France.
Oriel Instruments, "Introduction to Beam Splitters for Optical Research Applications", Apr. 2014, pp. 1-9, https://www.azoptics.com/Article aspx?ArticaID=871.
International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Arlilicial Stones For Research on the Mechinisms of Stone Breakage in Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'Nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologies, 2014, Pinnacle Biologies, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.

(56) References Cited

OTHER PUBLICATIONS

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.
Murray, A., et al. "Peripheral laser angioplasty with pulsed dye laser and ball tipped optical fibres", The Lancet, 1989, pp. 1471-1474, vol. 2, Issue 8678-8679.
Mohammadzadeh, M., et al. "Photoacoustic Shock Wave Emission and Cavitation from Structured Optical Fiber Tips", Applied Physics Letters, 2016, vol. 108, American Institute of Physics Publishing LLC.
Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.
Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.
Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.
Vogel, A., et al. "Plasma Formation in Water by Picosecond and Nanosecond Nd: YAG Laser Pulses—Part 1: Optical Breakdown at Threshold and Superthreshold Irradiance", IEEE Journal of Selected Topics in Quantum Electronics, 1996, pp. 847-859, vol. 2, No. 4, IEEE.
Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.
Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.
Lee, Seung H., et al. "Radial-firing optical fiber tip containing conical-shaped air-pocket for biomedical applications", Optics Express, 2015, vol. 23, No. 16, Optical Society of America.
Hui, C., et al. "Research on sound fields generated by laser-induced liquid breakdown", Optica Applicata, 2010, pp. 398-907, vol. XL, No. 4, Xi'an, China.
Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.
Roberts, Randy M., et al. "The Energy Partition of Underwater Sparks", The Journal of the Acoustical Society of America, 1996, pp. 3465-3475, vol. 99, No. 6, Acoustical Society of America.
Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.
Scepanovic, Obrad R., et al. "Multimodal spectroscopy detects features of vulnerable atherosclerotic plaque", Journal of Biomedical Optics, 2011, pp. 1-10, vol. 16, No. 1, SPIE.
Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.
Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.
Vogel, A., et al. "Shock-Wave Energy and Acoustic Energy Dissipation After Laser-induced Breakdown", SPIE, 1998, pp. 180-189, vol. 3254, SPIE.
International Search Report and Written Opinion dated Aug. 20, 2021 in PCT Application Serial No. PCT/US2021/031130.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.

(56) References Cited

OTHER PUBLICATIONS

Deckelbaum, Lawrence I., "Coronary Laser Angioplasty", Lasers in Surgery and Medicine, 1994, pp. 101-110, Wiley-Liss Inc.

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and on Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method for Fabricating Artificial Kidney Stones of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions,Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

International Search Report and Written Opinion dated Aug. 25, 2022 in PCT Application Serial No. PCTUS/2022/028035.

International Search Report and Written Opinion dated Sep. 15, 2022 in PCT Application Serial No. PCTUS/2022/032045.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

Medlight, "Cylindrical light diffuser Model RD-ML", Medlight S.A., Switzerland. 2015. (This reference was cited in a prior Information Disclosure Statement. However, the relevant date was missing. The date has now been added.).

Medlight, "Cylindircal light diffuser Model RD", Medlight S.A., Switzerland. 2015. (This reference was cited in a prior Information Disclosure Statement. However, the relevant date was missing. The date has now been added.).

Ohl, Siew-Wan, et al. "Bubbles with shock waves and ultrasound: a review", Interface Focus, pp. 1-15, vol. 5, The Royal Society Publishing Oct. 2015. (This reference was cited in a prior Information Disclosure Statement. However, the relevant date was missing. The date has now been added.).

Schafter+Kirchhoff, Laser Beam Couplers series 60SMS for coupling into single-mode and polarizationmaintaining fiber cables, Schafter+Kirchhoff, pp. 1-5, Germany. Dec. 2, 2021. (This reference was cited in a prior Information Disclosure Statement. However, the relevant date was missing. The date has now been added.).

Meng et al., "Accurate Recovery Of Atrial Endocardial Potential Maps From Non-contact Electrode Data." Auckland Bioengineering Institute. (ID 1421). May 2019. (This reference was cited in a prior Information Disclosure Statement. However, the relevant date was missing. The date has now been added.).

Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).

Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).

(56) References Cited

OTHER PUBLICATIONS

International Search Report and Written Opinion, PCT Application Serial No. PCT/US2022/047751 dated Feb. 10, 2023, by the European Patent Office.

* cited by examiner

ACOUSTIC PERFORMANCE MONITORING SYSTEM AND METHOD WITHIN INTRAVASCULAR LITHOTRIPSY DEVICE

RELATED APPLICATION

This application claims priority on U.S. Provisional Application Ser. No. 62/987,063, filed on Mar. 9, 2020. To the extent permitted, the contents of U.S. Provisional Application Ser. No. 62/987,063 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a catheter system for placement near a treatment site within or adjacent to a vessel wall or a heart valve. In various embodiments, the catheter system includes an energy source, an inflatable balloon, an energy guide, and an acoustic sensor. The energy source generates energy. The inflatable balloon is positionable substantially adjacent to the vascular lesion. The inflatable balloon has a balloon wall that defines a balloon interior that receives a balloon fluid. The energy guide is configured to receive energy from the energy source and guide the energy into the balloon interior. The acoustic sensor is positioned outside the body of the patient. The acoustic sensor is configured to sense acoustic sound waves generated in the balloon fluid within the balloon interior.

In some embodiments, the balloon fluid is provided to the balloon interior so that the inflatable balloon expands from a collapsed configuration to an expanded configuration.

In certain embodiments, the energy guide includes a photoacoustic transducer that is configured to convert the energy into an acoustic wave within the balloon interior near a guide distal end of the energy guide.

In some embodiments, the energy source generates pulses of energy that are guided along the energy guide into the balloon interior to induce plasma formation in the balloon fluid within the balloon interior. Additionally, in such embodiments, the plasma formation can cause rapid bubble formation and can impart pressure waves upon the balloon wall adjacent to the vascular lesion. Moreover, in such embodiments, the plasma formation, the bubble formation and the imparted pressure waves can generate acoustic sound waves in the balloon fluid within the balloon interior within predetermined acoustic frequency and amplitude thresholds during normal operation of the catheter system.

In various embodiments, the acoustic sensor generates a sensor signal based at least in part on the sensed acoustic sound waves generated in the balloon fluid within the balloon interior. In some such embodiments, the catheter system further includes a system controller that is electrically coupled to the acoustic sensor, the system controller being configured to receive the sensor signal from the acoustic sensor and to control operation of the catheter system based at least in part on the sensor signal. In alternative embodiments, the acoustic sensor can be electrically coupled to the system controller via a wired connection, or the acoustic sensor can be electrically coupled to the system controller via a wireless connection.

In certain embodiments, the system controller is configured to recognize normal operation of the catheter system based at least in part on the sensor signal. Further, in some embodiments, the system controller is configured to recognize potential damage to the energy guide based at least in part on the sensor signal. Moreover, in certain such embodiments, the system controller is configured to automatically shut down operation of the catheter system upon recognition of potential damage to the energy guide.

In some embodiments, normal operation of the catheter system generates acoustic sound waves in the balloon fluid within the balloon interior within predetermined acoustic frequency and amplitude thresholds. In such embodiments, the system controller can be configured to compare acoustic frequencies and amplitudes within the sensed acoustic sound waves from the sensor signal with the predetermined frequency and amplitude thresholds to determine if the sensed acoustic sound waves are outside a normal operating range.

In certain embodiments, the acoustic sensor is positioned adjacent to the system controller.

In some embodiments, at least a portion of the system controller is positioned within a system console. In such embodiments, the acoustic sensor can be positioned adjacent to the system console.

In various embodiments, the catheter system further includes a handle assembly that is coupled to the balloon, the handle assembly being usable by a user to operate the catheter system. In some such embodiments, the acoustic sensor is positioned adjacent to the handle assembly. Still further, in certain such embodiments, at least a portion of the system controller can be positioned within the handle assembly.

In some embodiments, the acoustic sensor is positioned adjacent to the body of the patient.

In certain embodiments, the energy source includes a laser.

In some embodiments, the energy guide includes an optical fiber.

In various embodiments, the energy guide includes an electrode pair including spaced apart electrodes that extend into the balloon interior, and pulses of high voltage from the energy source are applied to the electrodes and form an electrical arc across the electrodes.

In certain applications, the present invention is further directed toward a method for treating a vascular lesion within or adjacent to a vessel wall within a body of a patient, the method including the steps of generating energy with an energy source; positioning a balloon substantially adjacent to the vascular lesion, the balloon having a balloon wall that defines a balloon interior that receives a balloon fluid; receiving energy from the energy source with an energy guide and guiding the energy with the energy guide into the balloon interior; and sensing acoustic sound waves generated in the balloon fluid within the balloon interior with an acoustic sensor, the acoustic sensor being positioned outside the body of the patient.

In some embodiments, the method further includes the step of converting the energy into an acoustic wave within the balloon interior with a photoacoustic transducer that is positioned near a guide distal end of the energy guide.

In certain embodiments, the step of generating includes generating pulses of energy with the energy source, and the step of guiding includes guiding the pulses of energy along the energy guide into the balloon interior to induce plasma formation in the balloon fluid within the balloon interior to cause rapid bubble formation and to impart pressuring waves upon the balloon wall adjacent to the treatment site.

In various embodiments, the step of guiding includes the plasma formation, the bubble formation and the imparted pressure waves generating acoustic sound waves in the balloon fluid within the balloon interior within predetermined acoustic frequency and amplitude thresholds during normal operation of the catheter system.

In some embodiments, the method also includes the step of generating a sensor signal with the acoustic sensor based at least in part on the sensed acoustic sound waves generated in the balloon fluid within the balloon interior.

In certain embodiments, the method also includes the steps of electrically coupling a system controller to the acoustic sensor; receiving the sensor signal from the acoustic sensor with the system controller; and controlling operation of the catheter system with the system controller based at least in part on the sensor signal.

In various embodiments, the method also includes the steps of recognizing potential damage to the energy guide with the system controller based at least in part on the sensor signal, and automatically shutting down operation of the catheter system with the system controller upon recognition of potential damage to the energy guide.

In some embodiments, the step of generating includes the energy source being a laser, and the step of receiving includes the energy guide including an optical fiber.

In certain embodiments, the step of generating energy includes the energy source generating electrical impulses.

In various embodiments, the step of receiving includes the energy guide including an electrode pair including spaced apart electrodes that extend into the balloon interior; and further comprising the step of applying pulses of high voltage from the energy source to the electrodes to form an electrical arc across the electrodes.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
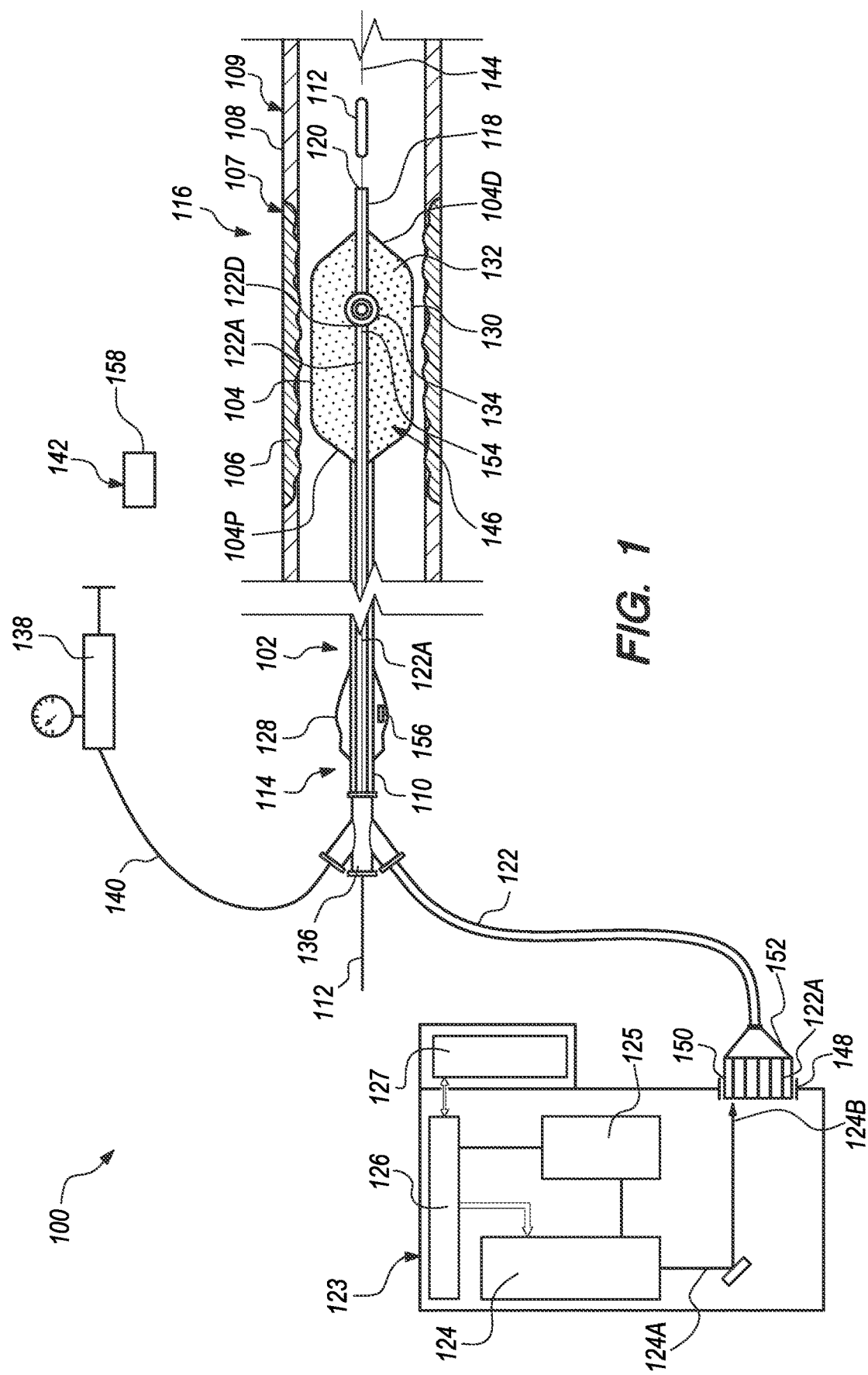
FIG. 1 is a schematic cross-sectional view of an embodiment of a catheter system in accordance with various embodiments herein, the catheter system including a performance monitoring system having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

The catheter systems and related methods disclosed herein are configured to monitor the performance, reliability and safety of an intravascular lithotripsy catheter. In various embodiments, the catheter systems of the present invention utilize an energy source, which in certain embodiments can be an energy source such as a laser or any other suitable energy source, which provides energy that is guided by an energy guide to create a localized plasma in a balloon fluid within a balloon interior of an inflatable balloon of the catheter. In certain embodiments, the energy guide can be a light guide that guides light energy. It is understood, however, that light guides are but one type of energy guide, and any other type of energy guide can equally be used with the catheter systems provided herein. It is further understood that use of the terms "energy source", "light guide", and/or "light energy" is not intended to limit the scope of the inventions, but are merely provided for the sake of convenience and as representative examples.

The localized plasma, in turn, induces a high energy bubble inside the balloon interior to create pressure waves to impart pressure onto and induce fractures in a vascular lesion, such as a calcified vascular lesion or a fibrous vascular lesion, at a treatment site within or adjacent to a blood vessel wall or a heart valve. As used herein, the treatment site can include a vascular lesion such as a calcified vascular lesion or a fibrous vascular lesion, typically found in a blood vessel and/or a heart valve. Thus, the pressure waves can transfer mechanical energy through an incompressible balloon fluid to the treatment site to impart a fracture force on the intravascular lesion.

As described in detail herein, the catheter systems of the present invention include an acoustic sensor that is configured to provide real-time continuous monitoring of the acoustic sound waves coming from the plasma and/or the pressure wave/pressure wave within the balloon interior during energy delivery. Continuous monitoring of the acoustic sound waves generated from the pressure wave inside of the balloon will yield a unique frequency and amplitude associated with a 'normal' operation during energy delivery from the energy source to the balloon fluid within the balloon interior.

The acoustic sensor can provide a sensor signal to a system controller (or signal processor), which would condition the sensor signal from the acoustic sensor to look for the specific and unique acoustic frequencies and amplitudes that are associated with the pressure wave. The system controller would filter the sensor signal continuously to monitor the sensor signal based on the energy application it sends to the catheter. If the acoustic parameters of the sensor signal over the course of one or more energy applications are measured outside the predetermined frequency and amplitude thresholds, i.e. outside the normal operating range, then it can be an indication of a number of potential failures in the overall system, including a broken or damaged energy guide, an issue within the catheter, and/or an issue with the system controller. In such situations, the system controller could then advise the operator to either stop the procedure, or perform a trouble shooting process (i.e. check laser connector etc.). The system controller could also send a signal to an onboard EEPROM of the catheter system to automatically shut down the catheter system, i.e. to make it inoperable.

It is appreciated that this real-time continuous monitoring of the acoustic sound waves coming from the plasma and/or the pressure wave within the balloon interior during energy delivery with the acoustic sensor provides valuable information to the user or operator as to the performance, reliability and safety of the catheter system. Specific examples of at least some issues that are addressed by the present invention can include, but are not limited to, one or more of: (1) audible detection of successful firing of the energy source, e.g., the laser source, to generate the plasma within the balloon interior, (2) audible detection of pressure waves being created within the balloon interior, i.e. upon bursting of the plasma bubbles, (3) audible detection of breakage or malfunction of the energy guide inside the catheter system, and/or (4) acoustic monitoring of progression of the procedure and efficacy of treatment.

As used herein, the terms "intravascular lesion", "vascular lesion" and "treatment site" are used interchangeably unless otherwise noted. As such, the intravascular lesions and/or the vascular lesions are sometimes referred to herein simply as "lesions" and can include lesions located at or near blood vessels or heart valves.

Those of ordinary skill in the art will realize that the following detailed description of the present invention is illustrative only and is not intended to be in any way limiting.

Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more vascular lesions within or adjacent a vessel wall of a blood vessel and/or a heart valve. In the embodiment illustrated in FIG. 1, the catheter system 100 can include one or more of a catheter 102, an energy guide bundle 122 including one or more energy guides 122A, a source manifold 136, a fluid pump 138, a system console 123 including one or more of an energy source 124, a power source 125, a system controller 126, and a graphic user interface 127 (a "GUI"), a handle assembly 128, and a performance monitoring system 142.

The catheter 102 is configured to move to a treatment site 106 within or adjacent to a blood vessel 108 or heart valve within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. The catheter shaft 110 can further include an inflation lumen (not shown).

In some embodiments, the catheter 102 can have a distal end opening 120 and can accommodate and be tracked over the guidewire 112 as the catheter 102 is moved and positioned at or near the treatment site 106.

The catheter shaft 110 of the catheter 102 can be coupled to the one or more energy guides 122A of the energy guide bundle 122. In certain embodiments, the energy guides 122A can be in optical communication with the energy source 124. The energy guide(s) 122A can be disposed along the catheter shaft 110 and within the balloon 104.

In some embodiments, each energy guide 122A can be an optical fiber and the energy source 124 can be a laser. The energy source 124 can be in optical communication with the energy guides 122A at the proximal portion 114 of the catheter system 100.

In some embodiments, the catheter shaft 110 can be coupled to multiple energy guides 122A such as a first energy guide, a second energy guide, a third energy guide, etc., which can be disposed at any suitable positions about the guidewire lumen 118 and/or the catheter shaft 110. For example, in certain non-exclusive embodiments, two energy guides 122A can be spaced apart by approximately 180 degrees about the circumference of the guidewire lumen 118 and/or the catheter shaft 110; three energy guides 122A can be spaced apart by approximately 120 degrees about the circumference of the guidewire lumen 118 and/or the catheter shaft 110; or four energy guides 122A can be spaced apart by approximately 90 degrees about the circumference of the guidewire lumen 118 and/or the catheter shaft 110. Still alternatively, multiple energy guides 122A need not be uniformly spaced apart from one another about the circumference of the guidewire lumen 118 and/or the catheter shaft 110. More particularly, it is further appreciated that the energy guides 122A described herein can be disposed uniformly or non-uniformly about the guidewire lumen 118 and/or the catheter shaft 110 to achieve the desired effect in the desired locations.

The balloon 104 can include a balloon wall 130 that defines a balloon interior 146, and can be inflated with a balloon fluid 132 to expand from a collapsed configuration suitable for advancing the catheter 102 through a patient's vasculature, to an expanded configuration suitable for anchoring the catheter 102 in position relative to the treatment site 106. Stated in another manner, when the balloon 104 is in the expanded configuration, the balloon wall 130 of the balloon 104 is configured to be positioned substantially adjacent to the treatment site 106, i.e. to the vascular lesion(s). In some embodiments, the energy source 124 of the catheter system 100 can be configured to provide sub-millisecond pulses of light from the energy source 124 (which can be a light source in one such embodiment), along the energy guides 122A (which can be light guides in one such embodiment), to a location within the balloon interior 146 of the balloon 104, thereby inducing plasma formation in the balloon fluid 132 within the balloon interior 146 of the balloon 104. The plasma formation causes rapid bubble formation, and imparts pressure waves upon the treatment site 106. Exemplary plasma-induced bubbles are shown as bubbles 134 in FIG. 1.

It is appreciated that although the catheter systems 100 illustrated herein are sometimes described as including a light source 124 and one or more light guides 122A, the catheter system 100 can alternatively include any suitable energy source 124 and energy guides 122A for purposes of generating the desired plasma in the balloon fluid 132 within the balloon interior 146. For example, in one non-exclusive alternative embodiment, the energy source 124 can be configured to provide high voltage pulses, and each energy guide 122A can include an electrode pair including spaced apart electrodes that extend into the balloon interior 146. In such embodiment, each pulse of high voltage is applied to the electrodes and forms an electrical arc across the electrodes, which, in turn, forms the pressure waves within the balloon fluid 132 that are utilized to provide the fracture force onto the vascular lesions at the treatment site 106. Still alternatively, the energy source 124 and/or the energy guides 122A can have another suitable design and/or configuration.

The balloons 104 suitable for use in the catheter systems 100 described in detail herein include those that can be passed through the vasculature of a patient when in the collapsed configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pa., USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 12 mm in diameter. In some embodiments, the balloons 104 can include those having diameters ranging from at least one mm to five mm in diameter.

Additionally, in some embodiments, the balloons 104 herein can include those having a length ranging from at least five mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations within the treatment site 106.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen energy source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, $C_5F_{12}$).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 µm) of the electromagnetic spectrum. Suitable absorptive agents can include those with absorption maxima along the spectrum from at least ten nm to 2.5 µm. Alternatively, the balloon fluids 132 can include those that include absorptive agents that can selectively absorb light in the mid-infrared region (e.g., at least 2.5 µm to 15 µm), or the far-infrared region (e.g., at least 15 µm to one mm) of the electromagnetic spectrum. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG–emission maximum=1064 nm) lasers, holmium:YAG (Ho:YAG–emission maximum=2.1 µm) lasers, or erbium:YAG (Er:YAG–emission maximum=2.94 µm). In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the energy source 124. Various energy sources 124 having emission wavelengths of at least ten nanometers to one millimeter are discussed elsewhere herein.

It is appreciated that the catheter system 100 and/or the energy guide bundle 122 disclosed herein can include any number of energy guides 122A in optical communication with the energy source 124 at the proximal portion 114, and with the balloon fluid 132 within the balloon interior 146 of the balloon 104 at the distal portion 116. For example, in some embodiments, the catheter system 100 and/or the energy guide bundle 122 can include from one energy guide 122A to five energy guides 122A. In other embodiments, the catheter system 100 and/or the energy guide bundle 122 can include from five energy guides 122A to fifteen energy guides 122A. In yet other embodiments, the catheter system 100 and/or the energy guide bundle 122 can include from ten energy guides 122A to thirty energy guides 122A. Alternatively, in still other embodiments, the catheter system 100 and/or the energy guide bundle 122 can include greater than 30 energy guides 122A.

As noted above, the energy guides 122A can have any suitable design for purposes of generating plasma and/or pressure waves in the balloon fluid 132 within the balloon interior 146. Thus, the particular description of the energy guides 122A herein is not intended to be limiting in any manner, except for as set forth in the claims appended hereto.

In certain embodiments, the energy guides 122A herein can include an optical fiber or flexible light pipe. The energy guides 122A herein can be thin and flexible and can allow light signals to be sent with very little loss of strength. The energy guides 122A herein can include a core surrounded by a cladding about its circumference. In some embodiments, the core can be a cylindrical core or a partially cylindrical core. The core and cladding of the energy guides 122A can be formed from one or more materials, including but not limited to one or more types of glass, silica, or one or more polymers. The energy guides 122A may also include a protective coating, such as a polymer. It is appreciated that the index of refraction of the core will be greater than the index of refraction of the cladding.

In various embodiments, each energy guide 122A can guide light along its length to a distal portion, i.e. a guide distal end 122D, having at least one optical window (not shown) that is positioned within the balloon interior 146. The energy guides 122A can create a light path as a portion of an optical network including the energy source 124. The light path within the optical network allows light to travel from one part of the network to another. Both the optical fiber and the flexible light pipe can provide a light path within the optical networks herein.

Further, the energy guides 122A herein can assume many configurations about and/or relative to the catheter shaft 110 of the catheters 102 described herein. In some embodiments, the energy guides 122A can run parallel to the longitudinal axis 144 of the catheter shaft 110. In some embodiments, the energy guides 122A can be physically coupled to the catheter shaft 110. In other embodiments, the energy guides 122A can be disposed along a length of an outer diameter of the catheter shaft 110. In yet other embodiments, the energy guides 122A herein can be disposed within one or more energy guide lumens within the catheter shaft 110.

Additionally, it is further appreciated that the energy guides 122A can be disposed at any suitable positions about the circumference of the guidewire lumen 118 and/or the catheter shaft 110, and the guide distal end 122D of each of the energy guides 122A can be disposed at any suitable longitudinal position relative to the length of the balloon 104 and/or relative to the length of the guidewire lumen 118.

Further, the energy guides 122A herein can include one or more photoacoustic transducers 154, where each photoacoustic transducer 154 can be in optical communication with the energy guide 122A within which it is disposed. In some embodiments, the photoacoustic transducers 154 can be in optical communication with the guide distal end 122D of the energy guide 122A. Additionally, in such embodiments, the photoacoustic transducers 154 can have a shape that corresponds with and/or conforms to the guide distal end 122D of the energy guide 122A.

The photoacoustic transducer 154 is configured to convert energy into an acoustic wave at or near the guide distal end 122D of the energy guide 122A. It is appreciated that the direction of the acoustic wave can be tailored by changing an angle of the guide distal end 122D of the energy guide 122A.

It is further appreciated that the photoacoustic transducers 154 disposed at the guide distal end 122D of the energy guide 122A herein can assume the same shape as the guide distal end 122D of the energy guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the energy guide 122A can further include additional photoacoustic transducers 154 disposed along one or more side surfaces of the length of the energy guide 122A.

The energy guides 122A described herein can further include one or more diverting features or "diverters" (not shown in FIG. 1) within the energy guide 122A that are configured to direct light to exit the energy guide 122A toward a side surface e.g., at or near the guide distal end 122D of the energy guide 122A, and toward the balloon wall 130. A diverting feature can include any feature of the system herein that diverts light from the energy guide 122A away from its axial path toward a side surface of the energy guide 122A. Additionally, the energy guides 122A can each include one or more light windows disposed along the longitudinal or axial surfaces of each energy guide 122A and in optical communication with a diverting feature. Stated in another manner, the diverting features herein can be configured to direct light in the energy guide 122A toward a side surface, e.g., at or near the guide distal end 122D, where the side surface is in optical communication with a light window. The light windows can include a portion of the energy guide 122A that allows light to exit the energy guide 122A from within the energy guide 122A, such as a portion of the energy guide 122A lacking a cladding material on or about the energy guide 122A.

Examples of the diverting features suitable for use herein include a reflecting element, a refracting element, and a fiber diffuser. Additionally, the diverting features suitable for focusing light away from the tip of the energy guides 122A herein can include, but are not to be limited to, those having a convex surface, a gradient-index (GRIN) lens, and a mirror focus lens. Upon contact with the diverting feature, the light is diverted within the energy guide 122A to the photoacoustic transducer 154 that is in optical communication with a side surface of the energy guide 122A. As noted, the photoacoustic transducer 154 then converts energy into an acoustic wave that extends away from the side surface of the energy guide 122A.

The source manifold 136 can be positioned at or near the proximal portion 114 of the catheter system 100. The source manifold 136 can include one or more proximal end openings that can receive the plurality of energy guides 122A of the energy guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132 as needed.

As noted above, in the embodiment illustrated in FIG. 1, the system console 123 includes one or more of the energy source 124, the power source 125, the system controller 126, and the GUI 127. Alternatively, the system console 123 can include more components or fewer components than those specifically illustrated in FIG. 1. For example, in certain non-exclusive alternative embodiments, the system console 123 can be designed without the GUI 127. Still alternatively, one or more of the energy source 124, the power source 125, the system controller 126, and the GUI 127 can be provided within the catheter system 100 without the specific need for the system console 123.

Additionally, as shown, the system console 123, and the components included therewith, is operatively coupled to the catheter 102, the energy guide bundle 122, and the remainder of the catheter system 100. For example, in some embodiments, as illustrated in FIG. 1, the system console 123 can include a console connection aperture 148 (also sometimes referred to generally as a"socket") by which the energy guide bundle 122 is mechanically coupled to the system console 123. In such embodiments, the energy guide bundle 122 can include a guide coupling housing 150 (also sometimes referred to generally as a "ferrule") that houses a portion, e.g., a guide proximal end, of each of the energy guides 122A. The guide coupling housing 150 is configured to fit and be selectively retained within the console connection aperture 148 to provide the desired mechanical coupling between the energy guide bundle 122 and the system console 123.

Further, the energy guide bundle 122 can also include a guide bundler 152 (or "shell") that brings each of the individual energy guides 122A closer together so that the energy guides 122A and/or the energy guide bundle 122 can be in a more compact form as it extends with the catheter 102 into the blood vessel 108 during use of the catheter system 100.

As provided herein, the energy source 124 can be selectively and/or alternatively coupled in optical communication with each of the energy guides 122A in the energy guide bundle 122. In particular, the energy source 124 is configured to generate energy in the form of a source beam 124A, e.g., a pulsed source beam that can be selectively and/or alternatively directed to and received by each of the energy guides 122A in the energy guide bundle 122 as an individual guide beam 124B. Alternatively, the catheter system 100 can include more than one energy source 124. For example, in one non-exclusive alternative embodiment, the catheter system 100 can include a separate energy source 124 for each of the energy guides 122A in the energy guide bundle 122.

The energy source 124 can have any suitable design. In certain embodiments, as noted above, the energy source 124 can be configured to provide sub-millisecond pulses of light from the energy source 124 that are directed along the energy guides 122A, to a location within the balloon 104, thereby inducing plasma formation in the balloon fluid 132 within the balloon interior 146 of the balloon 104. The plasma formation causes rapid bubble formation, and imparts pressure waves upon the treatment site 106. In such embodiments, the sub-millisecond pulses of light from the energy source 124 can be delivered to the treatment site 106 at a frequency of between approximately one hertz (Hz) and 5000 Hz. In some embodiments, the sub-millisecond pulses of light from the energy source 124 can be delivered to the treatment site 106 at a frequency of between approximately 30 Hz and 1000 Hz. In other embodiments, the sub-millisecond pulses of light from the energy source 124 can be delivered to the treatment site 106 at a frequency of between approximately ten Hz and 100 Hz. In yet other embodiments, the sub-millisecond pulses of light from the energy source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the energy source 124 is typically utilized to provide pulses of energy, the energy source 124 can still be described as providing a single source beam 124A, i.e. a single pulsed source beam.

The energy sources 124 suitable for use herein can include various types of energy sources including lasers and lamps. Alternatively, as noted above, the energy sources 124, as referred to herein, can include any suitable type of energy source, such as a high voltage energy source that provides high voltage pulses of energy.

Suitable lasers can include short pulse lasers on the sub-millisecond timescale. In some embodiments, the energy source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 200 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the energy sources 124 suitable for use in the catheter systems 100 herein can include those capable of producing light at wavelengths of from at least 750 nm to 2000 nm. In other embodiments, the energy sources 124 can include those capable of producing light at wavelengths of from at least 700 nm to 3000 nm. In still other embodiments, the energy sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the energy source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the energy guides 122A when the catheter 102 is placed at the treatment site 106. In some embodiments, the pressure waves can be imparted upon the treatment site 106 from a distance within a range from at least ten mm to 20 mm extending radially from the energy guides 122A when the catheter 102 is placed at the treatment site 106. In other embodiments, the pressure waves can be imparted upon the treatment site 106 from a distance within a range from at least one mm to ten mm extending radially from the energy guides 122A when the catheter 102 is placed at the treatment site 106. In yet other embodiments, the pressure waves can be imparted upon the treatment site 106 from a distance within a range from at least 1.5 mm to four mm extending radially from the energy guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the energy source 124, the system controller 126, the GUI 127, the handle assembly 128, and the performance monitoring system 142. The power source 125 can have any suitable design for such purposes.

As noted, the system controller 126 is electrically coupled to and receives power from the power source 125. Additionally, the system controller 126 is coupled to and is configured to control operation of each of the energy source 124, the GUI 127 and the performance monitoring system 142. The system controller 126 can include one or more processors or circuits for purposes of controlling the operation of at least the energy source 124, the GUI 127 and the performance monitoring system 142. For example, the system controller 126 can control the energy source 124, e.g., the light source, for generating pulses of energy, e.g., light energy, as desired, e.g., at any desired firing rate. Additionally, the system controller 126 can control and/or operate in conjunction with the performance monitoring system 142 to effectively sense and/or monitor acoustic sound waves generated within the balloon interior 146 of the balloon 104 during energy delivery applications, i.e. to more effectively monitor the performance, reliability and safety of the catheter 102 and the catheter system 100. Further, in certain embodiments, the system controller 126 is configured to receive, process and integrate sensor output from the performance monitoring system 142 to determine and/or adjust for proper functioning of the catheter system 100. Stated in another manner, based at least in part on the sensor output from the performance monitoring system 142, the system controller 126 can determine that certain modifications to the functioning of the catheter system 100 are required. Further, the system controller 126 can also be configured to provide appropriate signals to the user via the GUI 137 in certain situations, e.g., when the performance monitoring system 142 provides evidence of potential breakage or malfunction of the energy guide 122A, potential issues with the catheter 102, and/or when the catheter system 100 is operating appropriately and effectively. Moreover, in some embodiments, the system controller 126 can be configured to automatically stop operation of the catheter system 100 when the sensor output dictates that such action would be appropriate.

Additionally, the system controller 126 can further be configured to control operation of other components of the catheter system 100, e.g., the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100. For example, in certain embodiments, an additional controller and/or a portion of the system controller 126 can be positioned and/or incorporated within the handle assembly 128.

The GUI 127 is accessible by the user or operator of the catheter system 100.

Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As shown in FIG. 1, the handle assembly 128 can be positioned at or near the proximal portion 114 of the catheter system 100, and/or near the source manifold 136. Additionally, in this embodiment, the handle assembly 128 is coupled to the balloon 104 and is positioned spaced apart from the balloon 104. Alternatively, the handle assembly 128 can be positioned at another suitable location.

The handle assembly 128 is handled and used by the user or operator to operate, position and control the catheter 102. The design and specific features of the handle assembly 128 can vary to suit the design requirements of the catheter system 100. In the embodiment illustrated in FIG. 1, the handle assembly 128 is separate from, but in electrical and/or fluid communication with one or more of the system controller 126, the energy source 124, the fluid pump 138, the GUI 127 and the performance monitoring system 142. In some embodiments, the handle assembly 128 can integrate and/or include at least a portion of the system controller 126 within an interior of the handle assembly 128. For example, as shown, in certain such embodiments, the handle assembly 128 can include circuitry 156 that can form at least a portion of the system controller 126. Additionally, in some embodiments, the circuitry 156 can receive electrical signals or data from the performance monitoring system 142, as described in greater detail herein below. Further, or in the alternative, the circuitry 156 can transmit such electrical signals or otherwise provide data to the system controller 126 as described herein.

In one embodiment, the circuitry 156 can include a printed circuit board having one or more integrated circuits, or any other suitable circuitry. In an alternative embodiment, the circuitry 156 can be omitted, or can be included within the system controller 126, which in various embodiments can be positioned outside of the handle assembly 128, e.g., within the system console 123. It is understood that the handle assembly 128 can include fewer or additional components than those specifically illustrated and described herein.

As described herein, the performance monitoring system 142 is configured to monitor the performance, reliability and safety of the catheter system 100. The design of the performance monitoring system 142 can be varied to suit the specific requirements of the catheter system 100. In various embodiments, as illustrated in FIG. 1, the performance monitoring system 142 can include an acoustic sensor 158 that is specifically configured to monitor and/or sense acoustic sound waves that are generated in the balloon fluid 132 within the balloon interior 146. Alternatively, the performance monitoring system 142 can include more components than those specifically illustrated and described in relation to FIG. 1.

As an overview, and as provided in greater detail herein, the performance monitoring system 142 and/or the acoustic sensor 158 is configured to provide real-time continuous monitoring of the acoustic sound waves coming from the plasma and/or the pressure wave in the balloon fluid 132 within the balloon interior 146 during energy delivery. As provided herein, the acoustic sound waves generated during firing of the energy source 124, during plasma generation in the balloon fluid 132 within the balloon interior 146, and during plasma burst, i.e. during pressure wave generation due to the bursting of the plasma bubbles, have a unique and specific sound signature with regard to various characteristics of the acoustic sound waves, e.g., in terms of frequency, velocity, amplitude, shape, timing, etc. The performance monitoring system 142 and/or the acoustic sensor 158 can be designed and/or programmed to listen for and identify such sound signatures. Thus, the performance monitoring system 142 and/or the acoustic sensor 158 are configured to listen for and identify what would be considered "normal" operation of the catheter system 100 during energy delivery from the energy source 124 to the balloon fluid 132 within the balloon interior 146.

Additionally, the acoustic sensor 158 can be electrically coupled to the system controller 126 and/or the circuitry 156, i.e. with a wired connection and/or with a wireless connection, for real-time signal measurement. The acoustic sensor 158 can generate and provide a sensor signal to the system controller 126 (or signal processor) or circuitry 156, which would condition the sensor signal from the acoustic sensor 158 to look for the specific and unique predetermined acoustic frequencies and amplitudes (i.e. predetermined acoustic frequency and amplitude thresholds) that are associated with the pressure wave. The system controller 126 and/or the circuitry 156 would filter the sensor signal continuously to monitor the sensor signal based on the laser energy application being sent to the catheter 102, i.e. to the balloon interior 146. Stated in another manner, the system controller 126 and/or the circuitry 156 are configured to compare the acoustic frequencies and amplitudes of the sensed acoustic sound waves, i.e. from the sensor signal, with the predetermined acoustic frequency and amplitude thresholds to determine if the acoustic sound waves generated in the balloon fluid 132 within the balloon interior 146 are outside the normal operating range. If the acoustic parameters of the sensor signal over the course of one or more energy applications are measured outside the predetermined frequency and amplitude thresholds, i.e. outside the normal operating range, then it can be an indication of a number of potential failures in the overall catheter system 100, including a broken or damaged energy guide 122A, an issue within the catheter 102, and/or an issue with the system controller 126.

It is appreciated that if the energy guide 122A breaks or is damaged during the use of the catheter system 100, energy delivery, e.g., laser energy delivery, must be stopped immediately. With the design of the performance monitoring system 142 and/or the acoustic sensor 158 described herein, the present invention detects any noted failures within the catheter system 100 and provides an indicator or signal that the system controller 126 can use to lock out the energy source 124. This provides a necessary safety interlock for a potentially hazardous condition in which the energy source 124 can leak out in an undesirable way. In particular, the sensor signal could be used to indicate to the surgeon, e.g., via the GUI 127, to halt the procedure and remove the catheter 102 from the patient 109 under treatment.

Additionally, with the design and operation of the performance monitoring system 142 illustrated and described herein, it is further appreciated that the system controller 126 and/or the circuitry 156 can also be considered to form a portion of the performance monitoring system 142.

As described in detail herein, the performance monitoring system 142 and/or the acoustic sensor 158 can be positioned in any suitable location outside the body 107 (also sometimes referred to herein as "extracorporeal") of the patient 109 for purposes of monitoring the acoustic sound waves generated in the balloon fluid 132 within the balloon interior 146. In one embodiment, the acoustic sensor 158 can be located on and/or adjacent to the patient 109 in a desirable area to maximize the efficiency of the sound signal. For example, the acoustic sensor 158 may be positioned on or underneath the sterile barrier (drape). Alternatively, the acoustic sensor 158 can be positioned in another suitable manner to effectively monitor the acoustic sound waves generated in the balloon fluid 132 within the balloon interior 146. For example, in certain non-exclusive alternative embodiments, the acoustic sensor 158 can be positioned inside and/or adjacent to the system console 123, adjacent to the system controller 126, inside and/or adjacent to the handle assembly 128, or in another suitable location.

Additionally, it is further appreciated that the acoustic sensor 158 can have any suitable design for purposes of accurately monitoring the acoustic sound waves that are generated in the balloon fluid 132 within the balloon interior 146.

Figure 2:
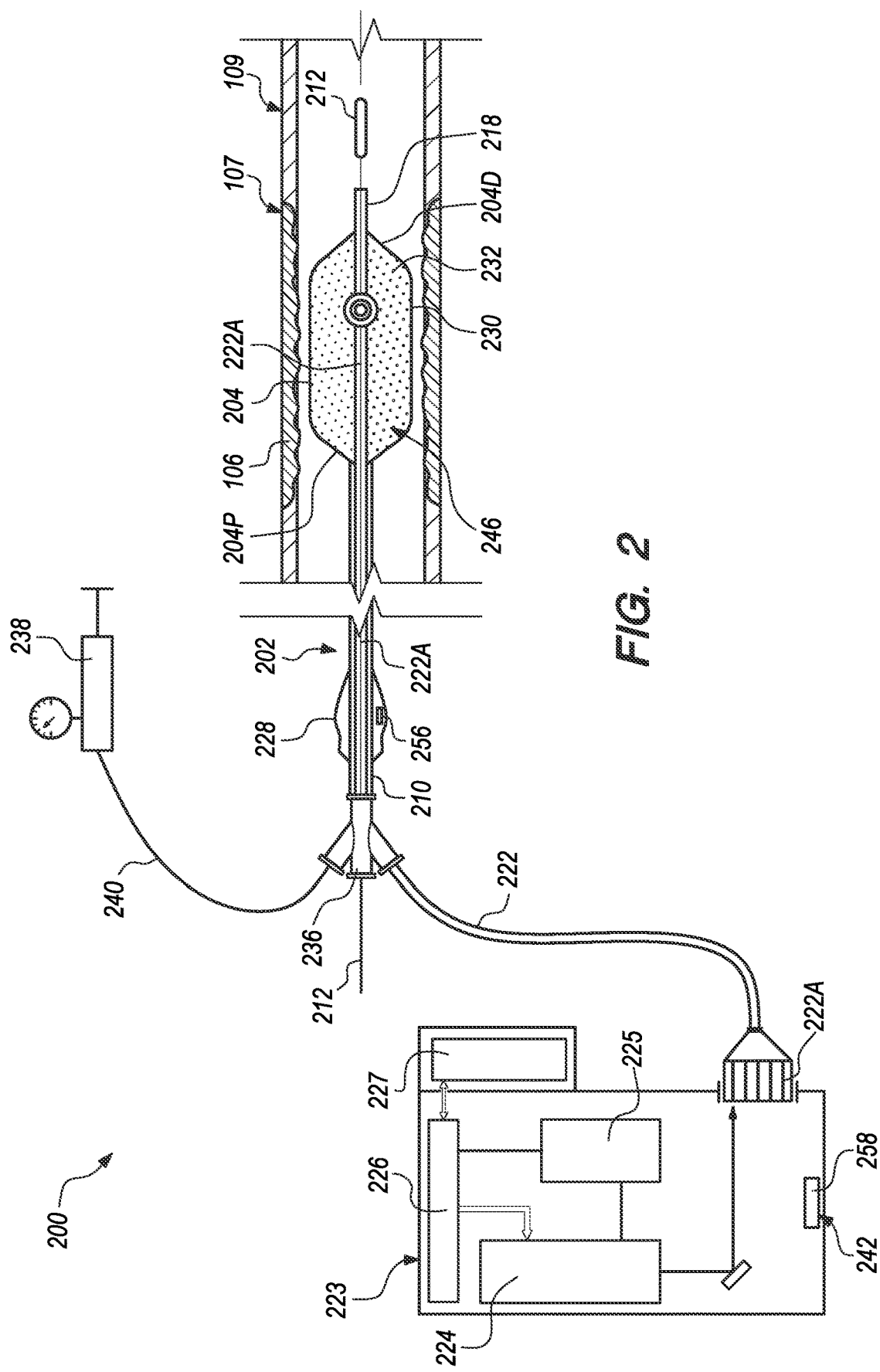
FIG. 2 is a schematic cross-sectional view of another embodiment of the catheter system including another embodiment of the performance monitoring system.

FIG. 2 is a schematic cross-sectional view of another embodiment of the catheter system 200 including another embodiment of the performance monitoring system 242.

The design of the catheter system 200 is substantially similar to the embodiment illustrated and described herein above. In particular, in the embodiment shown in FIG. 2, the catheter system 200 can again include a catheter 202 including a catheter shaft 210, a balloon 204 having a balloon wall 230 that defines a balloon interior 246, a balloon proximal end 204P, and a balloon distal end 204D, a balloon fluid 232 that is retained substantially within the balloon interior 246, a guidewire 212, and a guidewire lumen 218 that extends into the balloon interior 246; an energy guide bundle 222 including one or more energy guides 222A; a source manifold 236; a fluid pump 238; a system console 223 including one or more of an energy source 224, a power source 225, a system controller 226, and a GUI 227; a handle assembly 228; and the performance monitoring system 242. Alternatively, in other embodiments, the catheter system 200 can include more components or fewer components than what is specifically illustrated and described herein.

The catheter 202, including the catheter shaft 210, the balloon 204, the guidewire 212, and the guidewire lumen 218, is generally similar in design and operation to what has been described in detail herein above. Thus, such components will not be described in detail again in relation to the embodiment shown in FIG. 2.

As above, the balloon 204 is selectively movable between a collapsed configuration suitable for advancing the catheter 202 through a patient's vasculature, and an expanded configuration suitable for anchoring the catheter 202 in position relative to the treatment site 106. In some embodiments, the balloon proximal end 204P can be coupled to the catheter shaft 210, and the balloon distal end 204D can be coupled to the guidewire lumen 218. Additionally, the balloon 204 can be inflated with the balloon fluid 232, e.g., from the fluid pump 238, that is directed into the balloon interior 246 of the balloon 204 via the inflation conduit 240.

Additionally, the energy guide bundle 222 including the one or more energy guides 222A, and the system console 223 including one or more of the energy source 224, the power source 225, the system controller 226, and the GUI 227, are generally similar in design and operation to what has been described in detail herein above. Accordingly, such components will not be described in detail again in relation to the embodiment shown in FIG. 2.

Further, as above, the handle assembly 228 is handled and used by the user or operator to operate, position and control the catheter 202. Additionally, as shown in the embodiment illustrated in FIG. 2, the handle assembly 228 can again include circuitry 256 that can form a portion of the system controller 226. Alternatively, the handle assembly 228 can be configured without the circuitry 256.

As with the previous embodiment, the performance monitoring system 242 is again configured to monitor the performance, reliability and safety of the catheter system 200.

Additionally, the design of the performance monitoring system 242 can be somewhat similar to what was illustrated and described herein above in relation to the embodiment shown in FIG. 1. For example, the performance monitoring system 242 can again include an acoustic sensor 258 that is specifically configured to monitor and/or sense acoustic sound waves that are generated in the balloon fluid 232 within the balloon interior 246 during operation of the catheter system 200. More particularly, the acoustic sensor 258 can again be designed and/or programmed to listen for and identify particular sound signatures from such acoustic sound waves, e.g., during firing of the energy source 224, during plasma generation in the balloon fluid 232 within the balloon interior 246, and during plasma burst, i.e. during pressure wave generation due to the bursting of the plasma bubbles.

Further, the acoustic sensor 258 can again be electrically coupled to the system controller 226 and/or the circuitry 256, with a wired connection and/or a wireless connection, for real-time signal measurement. More specifically, the acoustic sensor 258 can again generate and provide a sensor signal to the system controller 226 or circuitry 256, which would condition the sensor signal from the acoustic sensor 258 to look for the specific and unique predetermined acoustic frequencies and amplitudes (i.e. predetermined acoustic frequency and amplitude thresholds) that are associated with the normal operation of the catheter system 200. As such, the system controller 226 and/or the circuitry 256 would be further configured to identify situations where the sensor signal includes acoustic frequencies and amplitudes outside the normal operating range, which would thus provide an indication of potential failures in the overall catheter system 200.

However, in the embodiment shown in FIG. 2, the acoustic sensor 258 is positioned in another suitable location outside the body 107 of the patient 109 for purposes of monitoring the acoustic sound waves generated in the balloon fluid 232 within the balloon interior 246. In particular, as shown in FIG. 2, in this embodiment, the acoustic sensor 258 is positioned inside and/or adjacent to the system console 223.

Additionally, as above, it is further appreciated that the acoustic sensor 258 can have any suitable design for purposes of accurately monitoring the acoustic sound waves that are generated in the balloon fluid 232 within the balloon interior 246.

Figure 3:
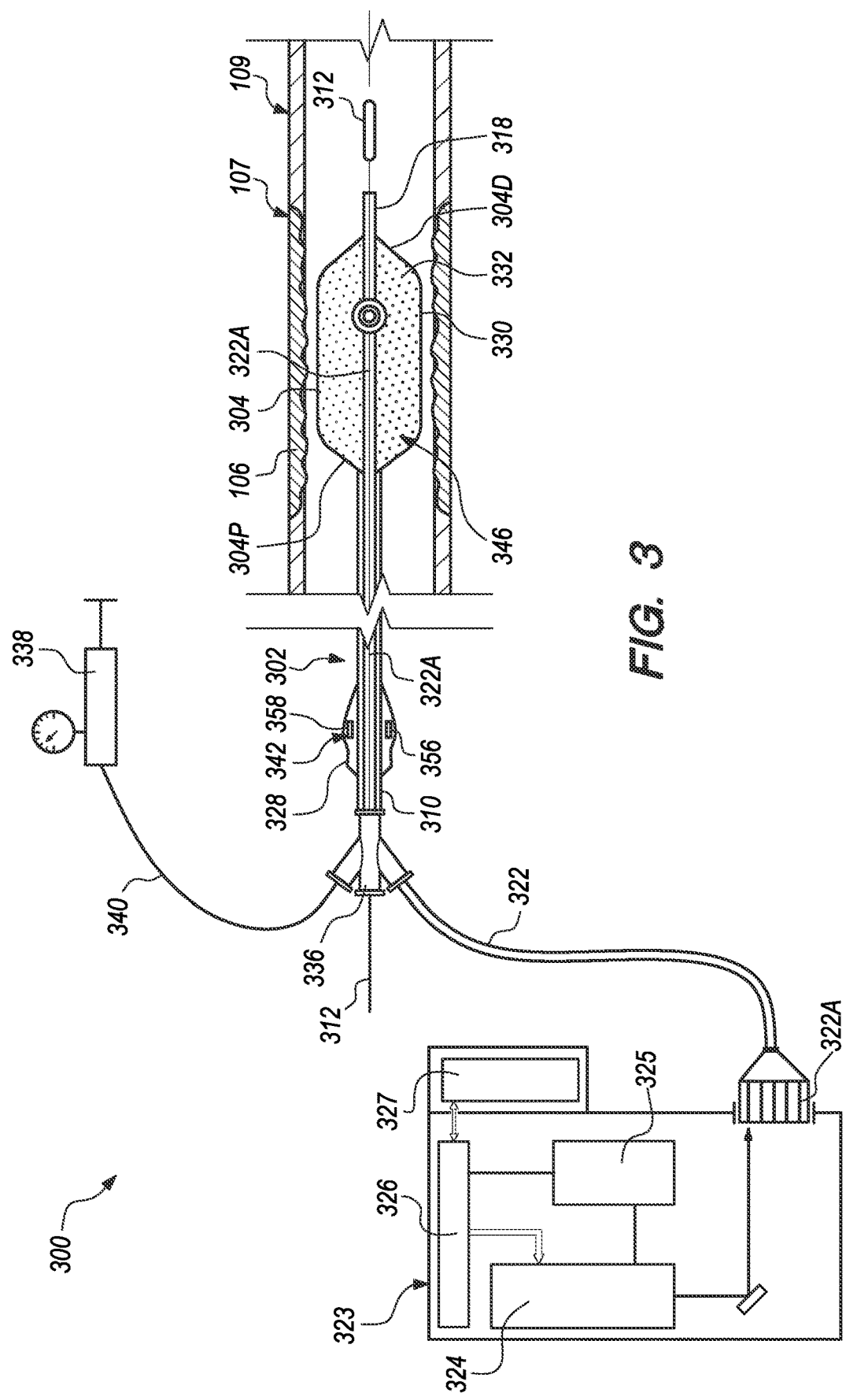
FIG. 3 is a schematic cross-sectional view of still another embodiment of the catheter system including still another embodiment of the performance monitoring system.

FIG. 3 is a schematic cross-sectional view of still another embodiment of the catheter system 300 including still another embodiment of the performance monitoring system 342. The design of the catheter system 300 is substantially similar to the embodiments illustrated and described herein above. In particular, in the embodiment shown in FIG. 3, the catheter system 300 can again include a catheter 302 including a catheter shaft 310, a balloon 304 having a balloon wall 330 that defines a balloon interior 346, a balloon proximal end 304P, and a balloon distal end 304D, a balloon fluid 332 that is retained substantially within the balloon interior 346, a guidewire 312, and a guidewire lumen 318 that extends into the balloon interior 346; an energy guide bundle 322 including one or more energy guides 322A; a source manifold 336; a fluid pump 338; a system console 323 including one or more of an energy source 324, a power source 325, a system controller 326, and a GUI 327; a handle assembly 328; and the performance monitoring system 342. Alternatively, in other embodiments, the catheter system 300 can include more components or fewer components than what is specifically illustrated and described herein.

The catheter 302, including the catheter shaft 310, the balloon 304, the guidewire 312, and the guidewire lumen 318, is generally similar in design and operation to what has been described in detail herein above. Thus, such components will not be described in detail again in relation to the embodiment shown in FIG. 3.

As above, the balloon 304 is selectively movable between a collapsed configuration suitable for advancing the catheter 302 through a patient's vasculature, and an expanded configuration suitable for anchoring the catheter 302 in position relative to the treatment site 106. In some embodiments, the balloon proximal end 304P can be coupled to the catheter shaft 310, and the balloon distal end 304D can be coupled to the guidewire lumen 318. Additionally, the balloon 304 can be inflated with the balloon fluid 332, e.g., from the fluid pump 338, that is directed into the balloon interior 346 of the balloon 304 via the inflation conduit 340.

Additionally, the energy guide bundle 322 including the one or more energy guides 322A, and the system console 323 including one or more of the energy source 324, the power source 325, the system controller 326, and the GUI 327, are generally similar in design and operation to what has been described in detail herein above. Accordingly, such components will not be described in detail again in relation to the embodiment shown in FIG. 3.

Further, as above, the handle assembly 328 is handled and used by the user or operator to operate, position and control the catheter 302. Additionally, as shown in the embodiment illustrated in FIG. 3, the handle assembly 328 can again include circuitry 356 that can form a portion of the system controller 326. Alternatively, the handle assembly 328 can be configured without the circuitry 356.

As with the previous embodiments, the performance monitoring system 342 is again configured to monitor the performance, reliability and safety of the catheter system 300. Additionally, the design of the performance monitoring system 342 can be somewhat similar to what was illustrated and described herein above in relation to the previous embodiments. For example, the performance monitoring system 342 can again include an acoustic sensor 358 that is specifically configured to monitor and/or sense acoustic sound waves that are generated in the balloon fluid 332 within the balloon interior 346 during operation of the catheter system 300. More particularly, the acoustic sensor 358 can again be designed and/or programmed to listen for and identify particular sound signatures from such acoustic sound waves, e.g., during firing of the energy source 324, during plasma generation in the balloon fluid 332 within the balloon interior 346, and during plasma burst, i.e. during pressure wave generation due to the bursting of the plasma bubbles.

Further, the acoustic sensor 358 can again be electrically coupled to the system controller 326 and/or the circuitry 356, with a wired connection and/or a wireless connection, for real-time signal measurement. More specifically, the acoustic sensor 358 can again generate and provide a sensor signal to the system controller 326 or circuitry 356, which would condition the sensor signal from the acoustic sensor 358 to look for the specific and unique predetermined acoustic frequencies and amplitudes (i.e. predetermined acoustic frequency and amplitude thresholds) that are associated with the normal operation of the catheter system 300. As such, the system controller 326 and/or the circuitry 356 would be further configured to identify situations where the sensor signal includes acoustic frequencies and amplitudes outside the normal operating range, which would thus provide an indication of potential failures in the overall catheter system 300.

However, in the embodiment shown in FIG. 3, the acoustic sensor 358 is positioned in another suitable location outside the body 107 of the patient 109 for purposes of monitoring the acoustic sound waves generated in the balloon fluid 332 within the balloon interior 346. In particular, as shown in FIG. 3, in this embodiment, the acoustic sensor 358 is positioned inside and/or adjacent to the handle assembly 328.

Additionally, as above, it is further appreciated that the acoustic sensor 358 can have any suitable design for purposes of accurately monitoring the acoustic sound waves that are generated in the balloon fluid 332 within the balloon interior 346.

As noted above, the performance monitoring system and/or the acoustic sensor of the present invention addresses several important challenges with the performance, reliability and safety of an intravascular lithotripsy catheter, in particular one that utilizes an energy source, e.g., a light source such as a laser source, to create a localized plasma which in turn induces a high energy bubble in the balloon fluid within the balloon interior of the balloon. For example, as noted above, issues that are addressed by the present invention include, but are not limited to: (1) audible detection of successful firing of the energy source, e.g., the laser source, to generate the plasma within the balloon interior, (2) audible detection of pressure waves being created within the balloon interior, i.e. upon bursting of the plasma bubbles, (3) audible detection of breakage or malfunction of the energy guide inside the catheter system, and (4) acoustic monitoring of progression of the procedure and efficacy of treatment.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques.

However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall or a heart valve within a body of a patient, the catheter system comprising:
   an energy source that generates energy;
   an inflatable balloon that is positionable substantially adjacent to the treatment site, the inflatable balloon having a balloon wall that defines a balloon interior, the balloon interior receiving a balloon fluid;
   an energy guide that is configured to receive energy from the energy source and guide the energy into the balloon interior;
   an acoustic sensor that is positioned outside of the body of the patient, the acoustic sensor being configured to sense acoustic sound waves generated in the balloon fluid within the balloon interior, the acoustic sensor generating a sensor signal based at least in part on the sensed acoustic sound waves generated in the balloon fluid within the balloon interior; and
   a system controller that is electrically coupled to the acoustic sensor, the system controller being configured to receive the sensor signal from the acoustic sensor and to control operation of the catheter system based at least in part on the sensor signal, the system controller being configured to recognize one of: (i) normal operation of the catheter system based at least in part on the sensor signal, and (ii) potential damage to the energy quid based at least in part on the sensor signal.

2. The catheter system of claim 1 wherein the energy guide includes a photoacoustic transducer that is configured to convert the energy into an acoustic wave within the balloon interior near a guide distal end of the energy guide.

3. The catheter system of claim 1 wherein the energy source generates pulses of energy that are guided along the energy guide into the balloon interior to induce plasma formation in the balloon fluid within the balloon interior, the plasma formation causing rapid bubble formation and imparting pressure waves upon the balloon wall adjacent to the treatment site.

4. The catheter system of claim 3 wherein the plasma formation, the bubble formation and the imparted pressure waves generate acoustic sound waves in the balloon fluid within the balloon interior within predetermined acoustic frequency and amplitude thresholds during normal operation of the catheter system.

5. The catheter system of claim 1 wherein the acoustic sensor is electrically coupled to the system controller via a wired connection.

6. The catheter system of claim 1 wherein the acoustic sensor is electrically coupled to the system controller via a wireless connection.

7. The catheter system of claim 1 wherein the system controller is configured to automatically shut down operation of the catheter system upon recognition of potential damage to the energy guide.

8. The catheter system of claim 1 wherein the energy source includes a laser.

9. The catheter system of claim 1 wherein the energy guide includes an optical fiber.

10. The catheter system of claim 1 wherein the energy guide includes an electrode pair including spaced apart electrodes that extend into the balloon interior, and pulses of high voltage from the energy source are applied to the electrodes and form an electrical arc across the electrodes.

11. The catheter system of claim 1 wherein the inflatable balloon has a drug eluting coating.

12. A catheter system for treating a treatment site within or adjacent to a vessel wall or a heart valve within a body of a patient, the catheter system comprising:
    a laser that generates energy;
    an inflatable balloon that is positionable substantially adjacent to the treatment site, the inflatable balloon having a balloon wall that defines a balloon interior, the balloon interior receiving a balloon fluid;
    an energy guide that is configured to receive energy from the energy source and guide the energy into the balloon interior, the energy source generating pulses of energy that are guided along the energy guide into the balloon interior to induce plasma formation in the balloon fluid within the balloon interior, the plasma formation causing rapid bubble formation and imparting pressure waves upon the balloon wall adjacent to the treatment site; and
    an acoustic sensor that is positioned outside of the body of the patient, the acoustic sensor being configured to sense acoustic sound waves generated in the balloon fluid within the balloon interior, the acoustic sensor generating a sensor signal based at least in part on the sensed acoustic sound waves generated in the balloon fluid within the balloon interior.

13. The catheter system of claim 12 further comprising a system controller that is electrically coupled to the acoustic sensor, the system controller being configured to receive the sensor signal from the acoustic sensor and to control operation of the catheter system based at least in part on the sensor signal.

14. The catheter system of claim 13 wherein the acoustic sensor is electrically coupled to the system controller via a wired connection.

15. The catheter system of claim 13 wherein the acoustic sensor is electrically coupled to the system controller via a wireless connection.

16. A catheter system for treating a treatment site within or adjacent to a vessel wall or a heart valve within a body of a patient, the catheter system comprising:
    an energy source that generates energy;
    an inflatable balloon that is positionable substantially adjacent to the treatment site, the inflatable balloon having a balloon wall that defines a balloon interior, the balloon interior receiving a balloon fluid;
    an energy guide that is configured to receive energy from the energy source and guide the energy into the balloon interior;
    an acoustic sensor that is positioned outside of the body of the patient, the acoustic sensor being configured to sense acoustic sound waves generated in the balloon fluid within the balloon interior, the acoustic sensor generating a sensor signal based at least in part on the sensed acoustic sound waves generated in the balloon fluid within the balloon interior;

a system controller that is electrically coupled to the acoustic sensor, the system controller being configured to receive the sensor signal from the acoustic sensor and to control operation of the catheter system based at least in part on the sensor signal;

wherein normal operation of the catheter system generates acoustic sound waves in the balloon fluid within the balloon interior within predetermined acoustic frequency and amplitude thresholds, and the system controller is configured to compare acoustic frequencies and amplitudes within the sensed acoustic sound waves from the sensor signal to the predetermined frequency and amplitude thresholds to determine if the sensed acoustic sound waves are outside a normal operating range.

17. The catheter system of claim 16 wherein the energy guide includes a photoacoustic transducer that is configured to convert the energy into an acoustic wave within the balloon interior near a guide distal end of the energy guide.

18. The catheter system of claim 16 wherein the energy source generates pulses of energy that are guided along the energy guide into the balloon interior to induce plasma formation in the balloon fluid within the balloon interior, the plasma formation causing rapid bubble formation and imparting pressure waves upon the balloon wall adjacent to the treatment site.

19. The catheter system of claim 16 wherein the energy source includes a laser.

20. The catheter system of claim 16 wherein the energy guide includes an optical fiber.

* * * * *